United States Patent
Zalevsky et al.

(10) Patent No.: US 10,175,392 B2
(45) Date of Patent: Jan. 8, 2019

(54) IMAGING SYSTEM WITH OPTIMIZED EXTENDED DEPTH OF FOCUS

(71) Applicant: Brien Holden Vision Institute, Kensington, New South Wales (AU)

(72) Inventors: Zeev Zalevsky, Rosh HaAyin (IL); Alex Zlotnik, Ashdod (IL); Ido Raveh, Neve Yarak (IL); Shai Ben-Yaish, Petach Tiqva (IL); Ofer Limon, Kfar-Saba (IL); Oren Yehezkel, Ramat-Gan (IL); Karen Lahav, Petach-Tikva (IL)

(73) Assignee: Brien Holden Vision Institute, Sydney, New South Wales (AU)

( * ) Notice: Subject to any disclaimer, the term of this patent is extended or adjusted under 35 U.S.C. 154(b) by 0 days.

(21) Appl. No.: 14/841,341

(22) Filed: Aug. 31, 2015

(65) Prior Publication Data
US 2015/0370066 A1 Dec. 24, 2015

Related U.S. Application Data

(63) Continuation of application No. 13/578,184, filed as application No. PCT/IL2011/000143 on Feb. 9, 2011,
(Continued)

(51) Int. Cl.
*G02B 27/42* (2006.01)
*G02B 3/00* (2006.01)
(Continued)

(52) U.S. Cl.
CPC .............. *G02B 3/0081* (2013.01); *A61F 2/16* (2013.01); *A61F 2/1648* (2013.01); *G02B 5/18* (2013.01);
(Continued)

(58) Field of Classification Search
CPC ................ G02B 27/00; G02B 27/0075; G02B 27/0025; G02B 27/0037; G02B 27/005;
(Continued)

(56) References Cited

U.S. PATENT DOCUMENTS

| 3,549,240 A | 12/1970 | Sawatari |
| 4,736,734 A | 4/1988 | Matsuura et al. |

(Continued)

FOREIGN PATENT DOCUMENTS

| CN | 101510012 A | 8/2009 |
| EP | 0369561 A2 | 5/1990 |

(Continued)

OTHER PUBLICATIONS

Zalevsky et al., "All-optical axial super resolving imaging using a low-frequency binary-phase mask," O[tics Express, Apr. 3, 206, pp. 2631-2643, vol. 14, No. 7, Optical Society of America (OSA), Washington, D.C., U.S.
(Continued)

*Primary Examiner* — Darryl J Collins
*Assistant Examiner* — Gary O'Neill
(74) *Attorney, Agent, or Firm* — Jones Day

(57) ABSTRACT

An optical processor is presented for applying optical processing to a light field passing through a predetermined imaging lens unit. The optical processor comprises a pattern in the form of spaced apart regions of different optical properties. The pattern is configured to define a phase coder, and a dispersion profile coder. The phase coder affects profiles of Through Focus Modulation Transfer Function (TFMTF) for different wavelength components of the light field in accordance with a predetermined profile of an extended depth of focusing to be obtained by the imaging lens unit. The dispersion profile coder is configured in accordance with the imaging lens unit and the predetermined
(Continued)

profile of the extended depth of focusing to provide a predetermined overlapping between said TFMTF profiles within said predetermined profile of the extended depth of focusing.

20 Claims, 7 Drawing Sheets

Related U.S. Application Data now Pat. No. 9,134,543, which is a continuation of application No. 12/781,428, filed on May 17, 2010, now Pat. No. 8,531,783.

(60) Provisional application No. 61/302,588, filed on Feb. 9, 2010.

(51) Int. Cl.
G02B 5/18 (2006.01)
G02C 7/04 (2006.01)
G02C 7/06 (2006.01)
G02B 27/00 (2006.01)
G02C 7/02 (2006.01)
A61F 2/16 (2006.01)

(52) U.S. Cl.
CPC ......... *G02B 5/1828* (2013.01); *G02B 5/1895* (2013.01); *G02B 27/0025* (2013.01); *G02B 27/0037* (2013.01); *G02B 27/0075* (2013.01); *G02B 27/4205* (2013.01); *G02B 27/4211* (2013.01); *G02C 7/022* (2013.01); *G02C 7/04* (2013.01); *G02C 7/049* (2013.01); *G02C 7/06* (2013.01); *A61F 2/1613* (2013.01); *G02C 2202/22* (2013.01); *Y10S 977/902* (2013.01); *Y10S 977/932* (2013.01)

(58) Field of Classification Search
CPC ............ G02B 27/0056; G02B 27/4211; G02B 2027/0127; G02B 3/0081; G02B 5/18; G02B 5/1828; G02B 5/1895; G02B 27/4205; A61F 2/1613; A61F 2/1637; A61F 2/1654; A61F 2/16; A61F 2/1648; G02C 7/022; G02C 7/04; G02C 7/049; G02C 7/06; G02C 2202/22; Y10S 977/902; Y10S 977/932
USPC ....... 359/558, 642, 738, 739, 740; 623/6.27, 623/6.3
See application file for complete search history.

(56) References Cited

U.S. PATENT DOCUMENTS

| | | |
|---|---|---|
| 4,923,296 A | 5/1990 | Erickson |
| 4,955,904 A | 9/1990 | Atebara et al. |
| 5,117,306 A | 5/1992 | Cohen |
| 5,158,572 A | 10/1992 | Nielsen |
| 5,172,143 A | 12/1992 | Baude et al. |
| 5,198,844 A | 3/1993 | Roffman et al. |
| 5,225,858 A | 7/1993 | Portney |
| 5,245,367 A | 9/1993 | Miller et al. |
| 5,260,727 A | 11/1993 | Oksman et al. |
| 5,299,062 A | 3/1994 | Ogata |
| 5,302,477 A | 4/1994 | Dao et al. |
| 5,482,801 A | 1/1996 | Smith et al. |
| 5,543,966 A | 8/1996 | Meyers |
| 5,662,706 A | 9/1997 | Legerton et al. |
| 5,674,282 A | 10/1997 | Cumming |
| 5,682,223 A | 10/1997 | Menezes et al. |
| 5,715,031 A | 2/1998 | Roffman et al. |
| 5,748,371 A | 5/1998 | Cathey, Jr. et al. |
| 5,757,458 A | 5/1998 | Miller et al. |
| 5,768,031 A | 6/1998 | Yang |
| 5,788,883 A | 8/1998 | Srivastava et al. |
| 5,822,091 A | 10/1998 | Baker |
| 5,864,379 A | 1/1999 | Dunn |
| 5,905,561 A | 5/1999 | Lee et al. |
| 5,965,330 A | 10/1999 | Evans et al. |
| 5,980,040 A | 11/1999 | Xu et al. |
| 6,024,447 A | 2/2000 | Portney |
| 6,069,738 A | 5/2000 | Cathey, Jr. et al. |
| 6,097,856 A | 8/2000 | Hammond, Jr. |
| 6,172,957 B1 | 1/2001 | Ogasawara |
| 6,366,405 B2 | 4/2002 | Abe |
| 6,429,972 B1 | 8/2002 | Ota et al. |
| 6,451,056 B1 | 9/2002 | Cumming |
| 6,474,814 B1 | 11/2002 | Griffin |
| 6,488,708 B2 | 12/2002 | Sarfarazi |
| 6,527,389 B2 | 3/2003 | Portney |
| 6,533,416 B1 | 3/2003 | Fermigier et al. |
| 6,536,898 B1 | 3/2003 | Cathey, Jr. |
| 6,537,317 B1 | 3/2003 | Steinert et al. |
| 6,554,424 B1 | 4/2003 | Miller et al. |
| 6,554,859 B1 | 4/2003 | Lang et al. |
| 6,576,012 B2 | 6/2003 | Lang |
| 6,661,816 B2 | 12/2003 | Delfyett et al. |
| 6,685,315 B1 | 2/2004 | De Carle |
| 7,025,454 B2 | 4/2006 | Cathey, Jr. |
| 7,061,693 B2 | 6/2006 | Zalevsky |
| 7,101,436 B2 | 9/2006 | Taniguchi et al. |
| 7,224,540 B2 | 5/2007 | Olmstead et al. |
| 7,365,917 B2 | 4/2008 | Zalevsky |
| 7,411,743 B2 | 8/2008 | Sugi |
| 7,569,312 B2 | 8/2009 | Misaka |
| 7,572,007 B2 | 8/2009 | Simpson |
| 7,646,549 B2 | 1/2010 | Zalevsky et al. |
| 7,859,769 B2 | 12/2010 | Zalevsky |
| 8,169,716 B2 | 5/2012 | Zalevsky et al. |
| 8,531,783 B2* | 9/2013 | Zalevsky ............. G02B 5/1895 359/558 |
| 8,913,331 B2 | 12/2014 | Zalevsky et al. |
| 9,134,543 B2 | 9/2015 | Zalevsky et al. |
| 2001/0055156 A1 | 12/2001 | Maruyama |
| 2003/0142268 A1 | 7/2003 | Miller et al. |
| 2003/0197906 A1 | 10/2003 | Furuta et al. |
| 2004/0114102 A1 | 6/2004 | Miller et al. |
| 2004/0114103 A1 | 6/2004 | Miller et al. |
| 2004/0141241 A1* | 7/2004 | Claytor ................... G02B 3/08 359/742 |
| 2004/0145808 A1 | 7/2004 | Cathey, Jr. et al. |
| 2004/0230299 A1 | 11/2004 | Simpson et al. |
| 2006/0082882 A1 | 4/2006 | Wang et al. |
| 2006/0176572 A1 | 8/2006 | Fiala |
| 2007/0258143 A1 | 11/2007 | Portney |
| 2008/0198482 A1 | 8/2008 | Zalevsky |
| 2008/0300679 A1 | 12/2008 | Altmann |
| 2009/0074239 A1 | 3/2009 | Zalevsky |
| 2009/0088840 A1 | 4/2009 | Simpson et al. |
| 2009/0112314 A1 | 4/2009 | Sarver et al. |
| 2009/0116096 A1 | 5/2009 | Zalevsky et al. |
| 2009/0147378 A1 | 6/2009 | Zalevsky et al. |
| 2009/0187242 A1 | 7/2009 | Weeber et al. |
| 2009/0234448 A1* | 9/2009 | Weeber ................. A61F 2/1613 623/6.3 |
| 2009/0279189 A1 | 11/2009 | Getman et al. |
| 2009/0303432 A1 | 12/2009 | Suzuki et al. |
| 2010/0075114 A1 | 3/2010 | Kurihara et al. |
| 2010/0149510 A1 | 6/2010 | Zaczek et al. |
| 2010/0295973 A1* | 11/2010 | Aubuchon ............. G02B 13/20 348/241 |
| 2011/0082541 A1 | 4/2011 | Zalevsky |
| 2011/0085050 A1* | 4/2011 | Dowski, Jr. ......... G02B 27/0075 348/222.1 |
| 2011/0149236 A1 | 6/2011 | Weeber |

FOREIGN PATENT DOCUMENTS

| | | |
|---|---|---|
| JP | 2137815 A | 5/1990 |
| WO | 99/57599 | 11/1999 |

(56) References Cited

FOREIGN PATENT DOCUMENTS

| WO | 01/35880 | 5/2001 | | |
|---|---|---|---|---|
| WO | 2003/012528 | 2/2003 | | |
| WO | 2003/032825 | 4/2003 | | |
| WO | 2003/052465 | 6/2003 | | |
| WO | 2003/052492 | 6/2003 | | |
| WO | 2003/076984 | 9/2003 | | |
| WO | 2004/113994 | 12/2004 | | |
| WO | WO2007122615 | A2 * | 11/2007 | ......... G02B 27/0075 |
| WO | WO 2007122615 | A2 * | 11/2007 | ......... G02B 27/0075 |
| WO | 2007/141788 | 12/2007 | | |
| WO | 2009/115932 | 9/2009 | | |
| WO | 2009/140080 | 11/2009 | | |
| WO | 2010/009254 | 1/2010 | | |

OTHER PUBLICATIONS

Kohn, A., "Visual adaptation: physiology, mechanisms, and functional benefits," J. Neurophysiol, Mar. 7, 2007, pp. 3155-3164, vol. 97.

M.A. Webster et al., "Neural Adjustments to Image Blur," National Neuroscience, Sep. 5, 2002, pp. 839-840 (Abstract).

K. Pesudovs & N.A. Brennan, "Decreased uncorrected vision after a period of distance fixation with spectacle wear," Optom. Vis. Sci. (Abstract).

O. Yehezkel et al., "Adaptation to astigmatic lens: effects on lateral interactions," Visual Sciences Society Annual Meeting, Sep. 15, 2005 (Abstract).

M. Webster et al., "Adapting to astigmatism," Journal of Vision, 2009, vol. 9(8): 986, 986a (Abstract).

E.B. Forrest, "Eye Scan Therapy for Astigmatism," Journal of the American Optometric Association, Dec. 1984, pp. 894-901, vol. 55(12) (Abstract).

T. Callina & T.P. Reynolds, "Traditional methods for the treatment of presbyopia: spectacles, contact lenses, bifocal contact lenses," Ophthalmology Clinics of North America, Mar. 2006, pp. 25-33, vol. 19(1) (Abstract).

C.W. Fowler & E.S. Pateras, "A gradient-index ophthalmic lens based on Wood's convex pseudo-lens," Ophthalmic and Physiological Optics, 1990, p. 262-270, vol. 10(3) (Abstract).

C. M. Sullivan & C.M. Fowler, "Progressive addition and variable focus lenses: a review," Ophthalmic and Physiological Optics, 1988, p. 402-414, vol. 8(4) (Abstract).

Di Feng et al., "Binary sub-wavelength diffractive lenses with long focal depth and high transverse resolution," Opt. Express, 2008, p. 20968-20973, vol. 16.

Joseph N. Mait et al., "Diffractive lens fabricated with binary features less than 60 nm," Opt. Lett., Mar. 15, 2000, pp. 381-83, vol. 25, No. 6.

Michael W. Farn, "Binary gratings with increased efficiency," Appl. Opt., 1992, pp. 4453-4458, vol. 31.

R. Petit & G. Bouchitte, "Replacement of a very fine grating by a stratified layer: homogenization techniques and the multiple-scale method," SPIE Proceedings Application and Theory of Periodic Structures, Diffraction Gratings, and Moire Phenomena III, 1987, pp. 25-31, vol. 815.

O. Yehezkel et al., "Learning to adapt: Dynamics of readaptation to geometrical distortions," Vision Research, 2010, pp. 1550-1558, vol. 50.

L.A. Carvalho, "A simple mathematical model for simulation of the human optical system based on in vivo corneal data," Revista Brasileira de Engenharia Biomedica, 2003, pp. 29-37, vol. 19, No. 1.

S. Bradburn et al., "Realizations of focus invariance in optical-digital systems with wave-front coding," Applied Optics, Dec. 10, 1997, pp. 9157-9166, vol. 36, No. 35, Optical Society of America.

A.R. Fitzgerrell et al., "Defocus transfer function for circularly symmetric pupils," Applied Optics, Aug. 10, 1997, pp. 5796-5804, vol. 23, No. 23, Optical Society of America.

C. Varamit et al., "Imaging properties of defocused partitioned pupils," Journal of the Optical Society of America, Jun. 1985, pp. 799-802, vol. 2, No. 6.

Eugene Hecht, "Optik," Dec. 31, 1989, pp. 441-445, Addison-Wesley Publishing Company.

H. Wang & F. Gan, "High focal depth with pure-phase adopizer," Applied Optics, Nov. 1, 2001, pp. 5658-5662, vol. 40, No. 31.

T.R.M. Sales et al., "Diffractive supperresolution elements," Journal of the Optical Society of America, Jul. 1997, pp. 1637-1646, vol. 14, No. 7.

D.M. De Juana et al., "Focusing properties of annular binary phase filters," Optics Communications, Jan. 2, 2004, pp. 71-77, vol. 229, No. 1-6, North-Holland Publishing Co., Amsterdam, NL.

M. Lim & C. Saloma, "Confocality condition in two-color excitation microscopy with two focused excitation beams," Optics Communications, Jun. 15, 2002, pp. 121-130, vol. 207, No. 1-6 (Abstract).

M.N. Akram & M.H. Asghar, "Step-zoom dual-field-of-view infra-red telescope," Applied Optics, May 1, 2003, pp. 2312-2316, vol. 42, No. 13, Optical Society of America (Abstract).

Hsin-Yu Tsai et al., "Reduction of focal-spot size using dichromats in absorbance modulation," Optics Letters, Dec. 15, 2008, pp. 2916-2918, vol. 33, No. 24 (Abstract).

Y.V. Vashchuk et al., "Reliable before-fabrication forecasting of expected surface slope distributions for x-ray optics," Optical Engineering, Apr. 11, 2012, vol. 51, No. 4 (Abstract).

\* cited by examiner

IMAGING SYSTEM WITH OPTIMIZED EXTENDED DEPTH OF FOCUS

This application is a continuation of U.S. patent application Ser. No. 13/578,184, which has a 371(c) date of Oct. 23, 2012, the entire contents of which are incorporated herein by reference. U.S. patent application Ser. No. 13/578,184 is a 371 national stage of International Application No. PCT/IL2011/000143 filed Feb. 9, 2011, which is a continuation of U.S. patent application Ser. No. 12/781,428 filed May 17, 2010, now U.S. Pat. No. 8,531,783, which International Application No. PCT/IL2011/000143 claims the benefit of U.S. Provisional Patent Application No. 61/302,588 filed Feb. 9, 2010.

FIELD OF THE INVENTION

This invention relates to an imaging system and method for imaging with extended depth of focus.

BACKGROUND OF THE INVENTION

Extension of the depth of focus of imaging is a common goal of various imaging systems. Techniques for extending the depth of focus of imaging systems have been developed, and are described for example in the following publications:

U.S. Pat. No. 6,536,898 and U.S. Pat. No. 7,025,454 disclose extended depth of field optics for human eye. This technique utilizes modification of contact lenses, intraocular implants, and/or the surface of the eye itself. This is accomplished by applying selected phase variations to these optical elements (e.g., by varying surface thickness of the cornea of the eye). The phase variations EDF-code the wavefront and cause the optical transfer function to remain essentially constant within a range of distances from the in-focus position. This provides a coded image on the retina. The human brain decodes this coded image, resulting in an in-focus image over an increased depth of field.

US 2009/0279189 describes a lens having extended depth of focus. The lens includes a plurality of lens layers, each lens layer being axi-symmetric and having an extended depth of focus to focus light in a corresponding section of a focal curve in the form of a straight line located on an optical axis. In the optical system, light is focused on an optical axis to obtain a clear image in a wide distance range between a camera and an object. The optical system has a point spread function that is simpler and more symmetric. That is, the optical system provides improved continuity of a lens surface and easiness and flexibility in optical designing.

U.S. Pat. Nos. 7,365,917, 7,061,693, WO 07/141788, all assigned to the assignee of the present application, describe all-optical techniques for extending the depth of focus being thus suitable for use in ophthalmic applications. According to these techniques, an imaging arrangement comprises an imaging lens having a certain affective aperture, and an optical element associated with said imaging lens. The optical element is configured as a phase-affecting, substantially non-diffractive optical element defining a spatially low frequency phase transition. The optical element and the imaging lens define a predetermined pattern formed by spaced-apart substantially optically transparent features of different optical properties.

GENERAL DESCRIPTION

The present invention provides a novel all-optical technique for appropriately extended depth of focus (EDOF) of an imaging lens unit. This technique utilizes a novel coding mechanism for coding a light field in the vicinity of an imaging lens unit. The present invention takes advantage of the earlier technique developed by the inventors and disclosed for example in the above-indicated patent publications U.S. Pat. Nos. 7,365,917, 7,061,693, WO 07/141788.

The main idea of the present invention is based on the understanding of the following: Imaging systems, such as human eye, have a depth of focus (DOF) determined by a number of physical parameters such as F/#, illumination spectrum and the aberrations terms (deviations from ideal imaging). For an aberration-free system, the DOF could be defined as follows (using Rayleigh 1/4 wave rule of thumb):

$$DOF = 4\lambda F/\#^2$$

where $F/\# = D/EFL$, EFL being the system effective focal length; and D is the system clear aperture.

Therefore, in order to extend the DOF of such an imaging system, the aperture of the imaging system is usually reduced, unavoidably resulting in the lost of energy and resolution. EDOF technology, developed by the inventors, utilizes phase-only coding (e.g. phase mask), having large spatial features (i.e. low spatial frequency phase transitions), located in the imaging system entrance pupil/aperture or plane/exit pupil in order to extend the DOF without reducing the aperture, i.e. causing neither loss of energy, nor loss of resolution. This technique eliminates a need for any image processing in order to restore the image.

Phase coding of the effective aperture of an imaging lens unit for extending the depth of focus of the lens unit results in a total profile of Through Focus Modulation Transfer Function (TFMTF) different from that of the original imaging lens unit, i.e. with no phase coding. Further details of lenses providing phase coding are given in the above indicated patents U.S. Pat. Nos. 7,061,693 and U.S. Pat. No. 7,365,917 assigned to the assignee of the present application, which are incorporated herein by reference in their entirety.

The inventors have found that the TFMTF profile defined by the EDOF-based phase coded imaging lens unit can be further optimized to obtain such a TFMTF profile, in which the TFMTF plot components corresponding to the desirably extended depth of focus for different wavelengths (wavelength ranges) overlap in the optimal way. The optimization comprises applying additional coding to the light field in the vicinity of the phase coded effective aperture of the imaging lens unit selected to take into account the EDOF effect to be obtained by the phase coding within the imaging lens unit, e.g. continuous range EDOF or discrete multi-range EDOF, and to compensate for longitudinal chromatic aberrations (LCA) of such EDOF imaging lens unit.

The LCA cause a shift in the extended focal position for different wavelengths, and could thus smear the performance of the EDOF-equipped imaging system. The invention provides for compensating for LCA effect while extending the depth of focusing of the imaging lens unit. To this end, the invention utilizes a dispersion profile coding (chromatic aberrations correction) of the light field which has been or is to be phase coded to thereby provide imaging with the desired profile of extended depth of focus for multiple wavelengths where the wavelengths' TFMTF profiles are desirably overlapping within the EDOF profile. The term "compensating for LCA" as used herein means reducing LCA for a lens relative to the same lens exclusive of the dispersion profile coding.

Thus, the present invention in its one broad aspect provides an all-optical processor for applying to a light field passing through a predetermined imaging lens unit, said optical processor comprising a pattern in the form of spaced apart regions of different optical properties, said pattern being configured to define: a phase coder affecting Through Focus Modulation Transfer Function profiles for different wavelength components of said light field in accordance with a predetermined profile of an extended depth of focusing of said light field passing through the imaging lens unit; and a dispersion profile coder configured to provide a predetermined overlapping between said profiles of the Through Focus Modulation Transfer Functions within said predetermined profile of the extended depth of focusing.

It should be noted that the present invention is not limited to "transmission mode" applications (such as ophthalmic applications), but is at the same time applicable to "reflective mode" imaging systems. In other words, the object and imaging planes may be located at the same side or at the opposite sides of the imaging lens unit. Accordingly, the term "imaging lens unit" should be interpreted broader than just one or more lenses, but also mirror or lens with reflective coating. Also, the term "TFMTF" should be referred to as through focus modulation transfer function.

The phase coder is implemented as a first pattern formed by a predetermined number of phase transitions, the phase transition being a region affecting a phase of light differently from that of its surroundings, while being substantially of the same transparency. The phase transition regions are arranged with a low spatial frequency within the lens aperture, so as to induce substantially non-diffractive phase effect onto the light field passing therethrough.

The dispersion profile coder is implemented as a second pattern, defining an arrangement of features such that this second pattern is substantially diffractive, and is configured to provide a predetermined optical power addition to the imaging lens unit. The optical power of the chromatic aberrations corrector (dispersion profile coder) is selected such that an imaging lens arrangement formed by said predetermined imaging lens unit, said phase coder and said dispersion profile coder is characterized by a desired dispersion profile.

In one embodiment of the invention, the first and second patterns are located at front and rear surfaces of the imaging lens unit, with respect to light propagation direction through the imaging lens unit. For example, the first and second patterns may be in the form of first and second surface reliefs on said front and rear surfaces of the imaging lens unit, respectively. According to another example, these may be phase mask and diffractive element located at the surface of the lens unit at a certain distances therefrom up to a physical contact. In yet another example, the first and second patterns may be incorporated in the lens unit, for example the phase coder pattern being formed by spaced-apart regions of a material having a refractive index different from that of the lens unit, and the dispersion profile coder being a diffractive pattern on one of the surfaces of the lens unit.

In another embodiment, the first and second patterns are configured as a surface relief on the same surface of the lens unit.

Thus, the first and second patterns may be defined by phase and diffractive masks associated with the lens unit, i.e. located at the same of opposites sides of the lens unit, or incorporated in the lens unit, or defining together a combined diffractive pattern comprising a superposition of said first and second patterns and being carried by the imaging lens unit.

According to another broad aspect of the invention, there is provided optical processor for processing light passing therethrough, comprising: an imaging lens unit providing optical power; a non-diffractive phase coder comprising an optical element that includes a pattern of spaced apart regions, said pattern being configured to affect a phase of light passing therethrough while substantially not effecting light diffraction and to provide an extended depth of focus for said lens, the imaging lens unit and said optical element being characterized by a Through Focus Modulation Transfer Function (TFMTF) for each of a plurality of different wavelength components of a light field passing therethrough; and a diffractive dispersion profile coder adapted to provide a reduction of chromatic aberration whereby there is greater overlap between the TFMTFs for the plurality of different wavelength components within the extended depth of focus.

The optical element and the dispersion profile coder may be disposed on the front and rear surfaces of the lens, respectively, or on the same surface of the imaging lens unit. At least one of the optical element and the dispersion profile coder may be incorporated in the imaging lens unit or an element of the imaging lens unit; or at least one of the optical element and the dispersion profile coder may be disposed at a location separated from the imaging lens unit or an element of the imaging lens unit. Yet another option is to combine the optical element and the dispersion profile coder as a superposition of a non-diffractive phase-affecting pattern of said optical element and a diffractive dispersion profile coder.

According to yet another broad aspect of the invention, there is provided an imaging lens carrying an optical processor adapted for extending the depth of focus with a predetermined dispersion profile.

The invention, in its yet further broad aspect, provides an imaging lens arrangement comprising an imaging lens unit and an optical processor associated with said imaging lens unit, the optical processor comprising a pattern of spaced-apart regions of different optical properties, said pattern comprising a phase coder affecting profiles of Through Focus Modulation Transfer Function (TFMTF) for different wavelength components of a light field being imaged in accordance with a predetermined profile of an extended depth of focusing to be obtained by said imaging lens arrangement; and a dispersion profile coder configured in accordance with the said imaging lens unit and said predetermined profile of the extended depth of focusing to provide a predetermined overlapping between said TFMTF profiles within said predetermined profile of the extended depth of focusing.

According to yet further broad aspect of the invention, there is provided an imaging lens comprising a pattern of spaced-apart regions of different optical properties, said pattern comprising a phase coder affecting profiles of Through Focus Modulation Transfer Function (TFMTF) for different wavelength components of a light field being imaged in accordance with a predetermined profile of an extended depth of focusing to be obtained by said imaging lens arrangement; and a dispersion profile coder configured in accordance with the said imaging lens unit and said predetermined profile of the extended depth of focusing to provide a predetermined overlapping between said TFMTF profiles within said predetermined profile of the extended depth of focusing.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A and 1B show the TFMTF graphs for different wavelengths (FIG. 1A) and a total TFMTF (FIG. 1B) for a single or multi-focal lens, and FIGS. 1C and 1D show similar graphs for a bi-focal lens;

FIG. 3A exemplifies an EDOF phase coding pattern, FIG. 3B exemplifies the dispersion profile coding pattern, and FIG. 3C shows a combined coding (pattern) applied to the light field propagating in the imaging lens arrangement; FIGS. 4A and 4B show respectively the dispersion of the TFMTF profiles for different wavelengths and the total TFMTF for a single- or multi-focal imaging lens and FIGS. 4C and 4D show similar graphs for a bifocal imaging lens.

DETAILED DESCRIPTION OF EMBODIMENTS

Figure 1A:
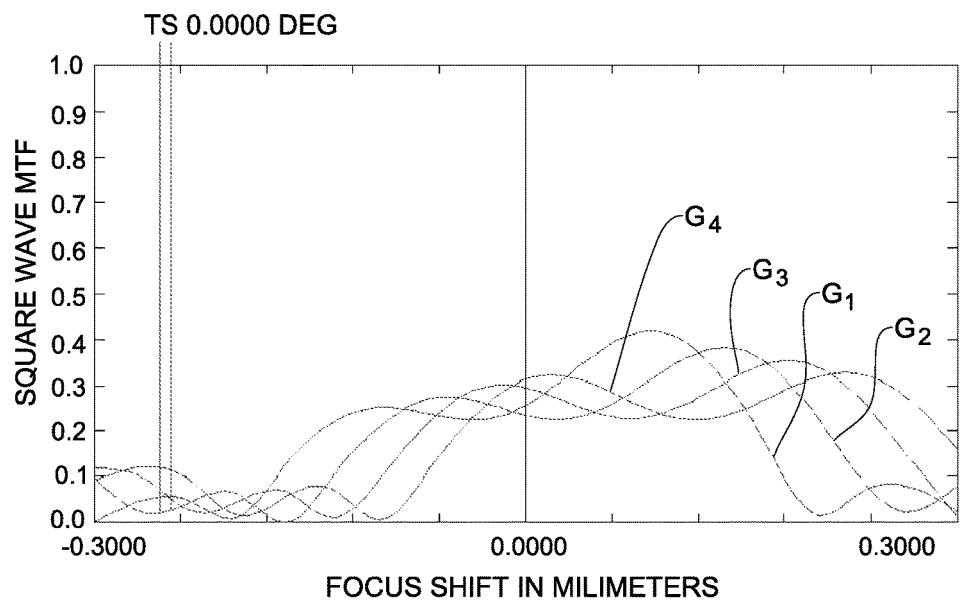
FIGS. 1A to 1D illustrate dispersion effects in an imaging lens.
Figure 1B:
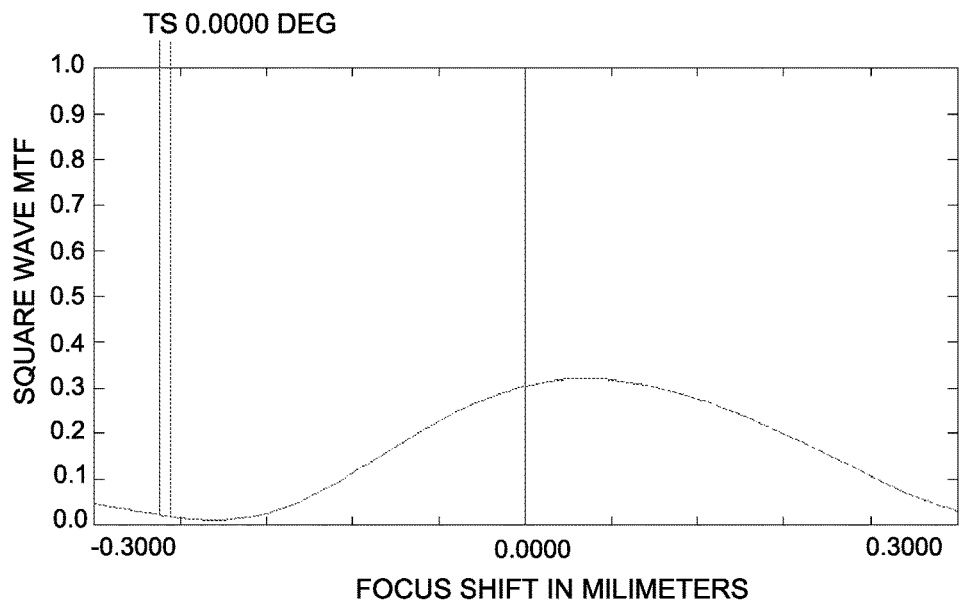
Figure 1C:
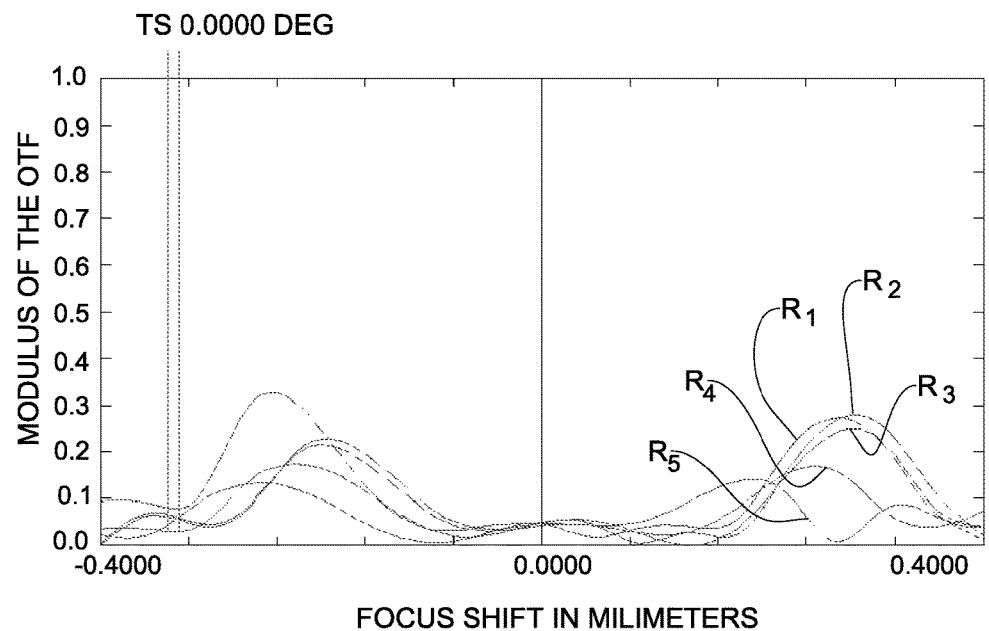
Figure 1D:
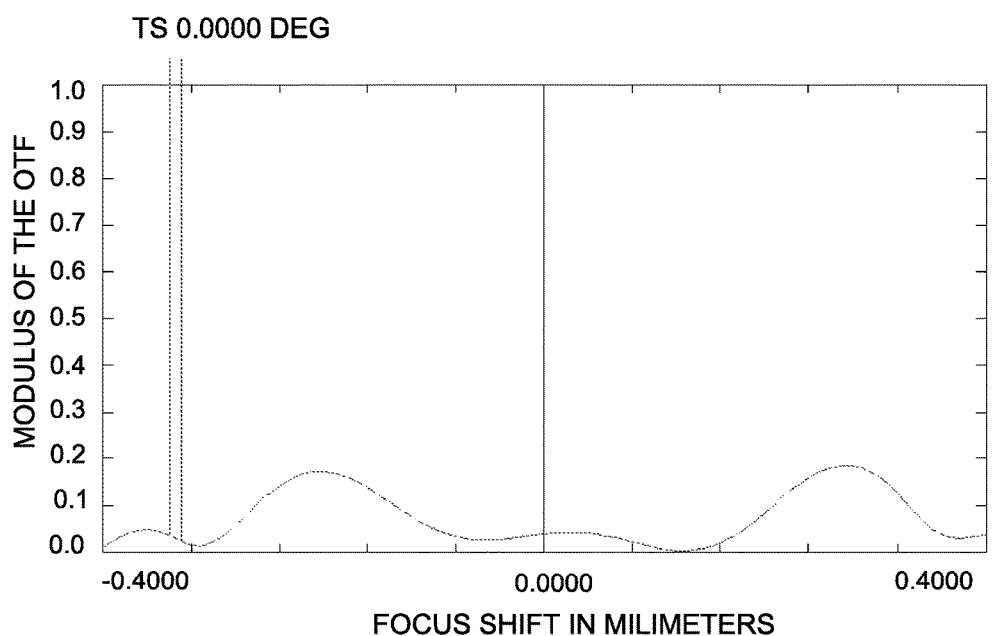

Reference is made to FIGS. 1A to 1D illustrating dispersion occurring in an imaging lens unit utilizing EDOF phase coding. The imaging lens unit may comprise a single-focus or multi-focus lens (FIGS. 1A and 1B) or a bi-focal lens (FIGS. 1C and 1D).

FIGS. 1A and 1C show the simulation results for a Through Focus Modulation Transfer Function (TFMTF) for 100 cyc/mm spatial frequency. This simulation was carried out with Zemax, using "Arizona Eye model", for a lens with a focal length of 16.7 mm and entrance pupil diameter of 3 mm.

In FIG. 1A, four TFMTF graphs are shown, $G_1$-$G_4$, corresponding to four different wavelengths in the range 0.5-0.6 μm. As shown, there is a relative shift for each wavelength: the plot for wavelength 0.6 μm is shifted 0.18 mm away from the corresponding graph for wavelength of 0.5 μm. In FIG. 1C, five TFMTF graphs $R_1$-$R_5$ are shown corresponding to passage of light of five different wavelengths in the range of 0.47-0.63 μm through a diffractive bi-focal lens unit. This graphs show TFMTF, being modulus of the OTF (i.e. imaging contrast) as a function of focus shift of the lens. Assuming all wavelengths are weighted the same (are of the same intensity), the resulted plots are illustrated in FIGS. 1B and 1D respectively.

Thus, for a given value of the TFMTF, the actual obtainable depth of focus (i.e. providing sufficient contrast of the image) is smaller than that for each wavelength. For example, for TFMTF=0.2, about 6 mm focal depth is obtained for each wavelength (FIG. 1A), while being about 4 mm for the total TFMTF plot (FIG. 1B).

Hence, there is a need to compensate the dispersion such as to cause the TFMTF plots overlap in the optimal way. It should be understood that the optimal way of overlapping means overlap within the required depth of focus region(s), defined by the specific applications. This may be one continuous region, or dual- or multi-region depth of focus as for example required in some ophthalmic applications or for imagers requiring improved image quality in the near and far vision zones.

The required compensation should take into account that DOF extensions for different wavelengths are different, i.e. larger for longer wavelength and smaller for shorter one, and should also take into account the initial depth of focus requirements with respect to a specific imaging lens unit. In other words, the chromatic aberrations correction (dispersion profile coding) should be configured in accordance with the depth of focus profiles, of the imaging lens with the EDOF effect, for the multiple wavelengths, e.g. those of the primary colors.

The present invention solves the above problem by providing an all-optical processor to be applied to a light field incident onto a predetermined imaging lens unit (e.g. passing through the lens unit). This optical processing is implemented by passing light through a pattern of spaced apart regions of different optical properties. This pattern defines a phase coder affecting TFMTF profiles for different wavelength components in accordance with predetermined EDOF profiles for certain imaging lens unit, and also defines a dispersion profile coder configured to provide a predetermined overlapping between the TFMTF profiles within the EDOF profile.

Figure 2A:
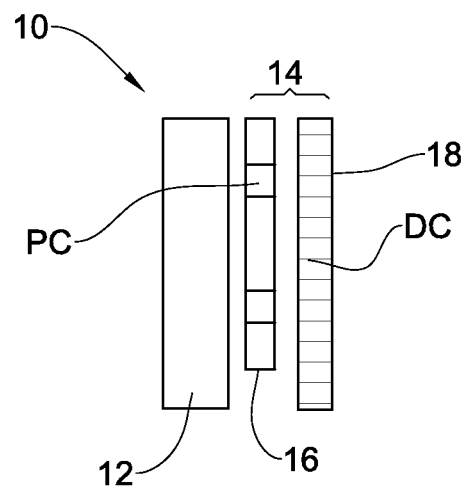
FIG. 2A shows schematically an imaging lens arrangement of the present invention.

Reference is made to FIG. 2A showing schematically an imaging arrangement 10 of the present invention. The imaging arrangement 10 includes an imaging lens unit 12 and an optical processor 14. The imaging lens unit 12 may include one or more optical elements configured and operable to create an image of an object in an imaging plane. The optical processor 14 may be a separate unit located close to (up to physical contact with) the imaging lens unit 12 (generally located so as to be in the vicinity of the effective aperture of the lens unit) located at either sides of the lens unit or both of them; or may be at least partially incorporated within the lens unit (embedded therein). The optical processor is configured to provide a desired profile of the extended depth of focus for the given imaging lens unit and a desired TFMTF profiles of multiple wavelengths within said profile of the extended depth of focus.

As shown in FIG. 2A, the optical processor 14 includes a phase coder (mask) 16 defined by a first pattern PC, and a dispersion profile coder 18 (e.g. mask) defined by a second pattern DC. In this example, the masks 16 and 18 are shown as being separate elements both separated from the lens unit, the phase coding mask 16 being located upstream of the lens unit and the dispersion coding mask 18 being located downstream of the lens with respect to the light propagation direction. It should however be noted that for the purposes of the invention the lens 12 and the coders 16, 18 may be arranged differently. Also, the codes of masks 16 and 18 may be integrated in a single pattern (mask) being separated from the lens or being integral therewith (e.g. embedded therein).

It should be understood that the imaging arrangement 10 is configured with one or more optical powers, to provide predetermined extension profile for the focus (focii) defined by said optical power, and to have a desired chromatic dispersion profile. The phase coder is configured to provide said predetermined extension profile, while substantially not adding any optical power to the lens unit. The desired optical power of the entire imaging arrangement for each wavelength is a sum of the respective optical powers of the elements of such arrangement. The dispersion coder is thus configured with a certain optical power (for each wavelength) selected such that the dispersion coder provides desirable shifts of the TFMTFs within the predetermined depth of focus extension profile. It should be understood that desired TFMTFs may be multi-lobe functions. Accordingly, for the given imaging lens with EDOF assembly, different dispersion codings might be used in order to achieve the desired overlap between different wavelength lobes.

Figure 2B:
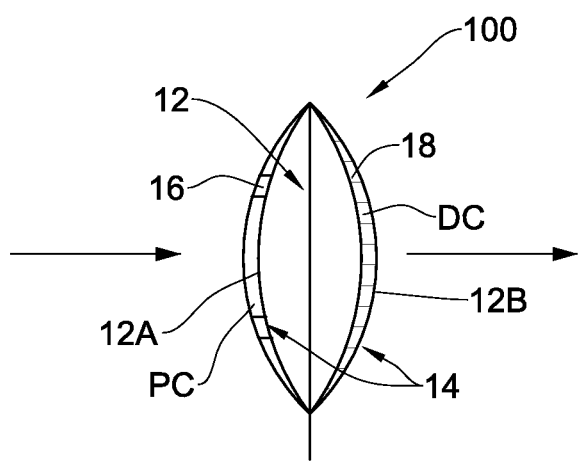
FIG. 2B shows a specific example of the implementation of the imaging arrangement of FIG. 2A.

FIG. 2B illustrates schematically an imaging arrangement 100 according to an example of the invention. The same reference numbers identify components common in all examples. The imaging arrangement 100 includes an imaging lens unit 12 (formed by a single lens in the present example), and an optical processor 14 which is carried by opposite sides 12A and 12B of the lens unit. Here, the phase and dispersion coders (patterns PC and DC) are implemented as surface patterns on the lens unit rear and front surfaces 12A and 12B. One of these patterns or both may be in the form of a surface relief; or may be formed by spaced-apart regions of a material having refractive index different from that of the lens.

Figure 3A:
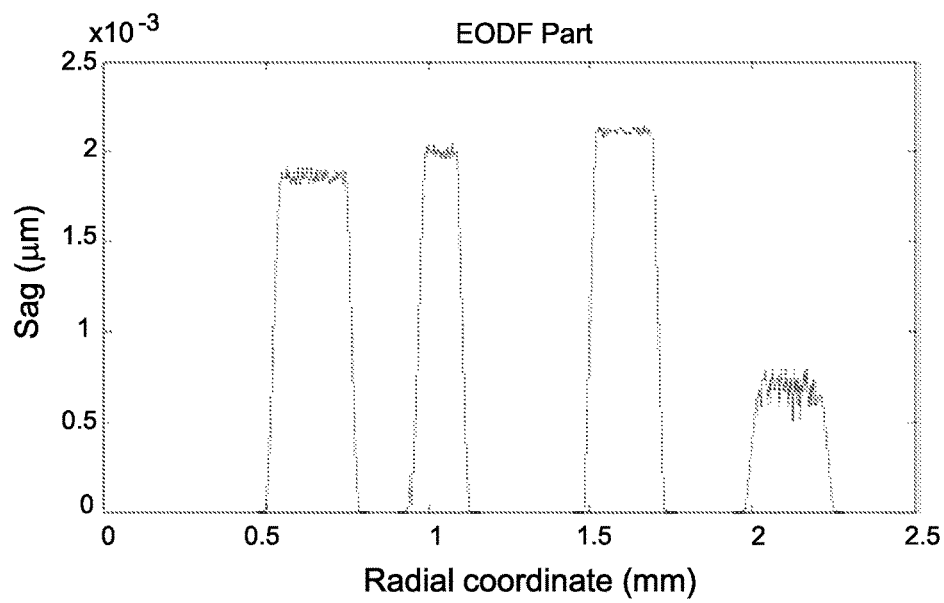
FIGS. 3A-3C exemplify the light field coding technique of the invention.
Figure 3B:
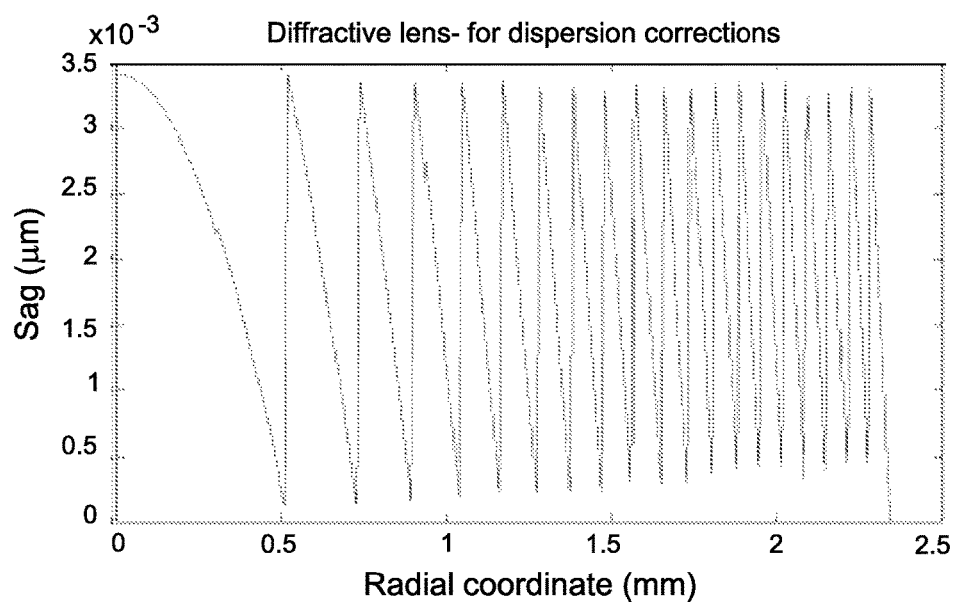
Figure 3C:
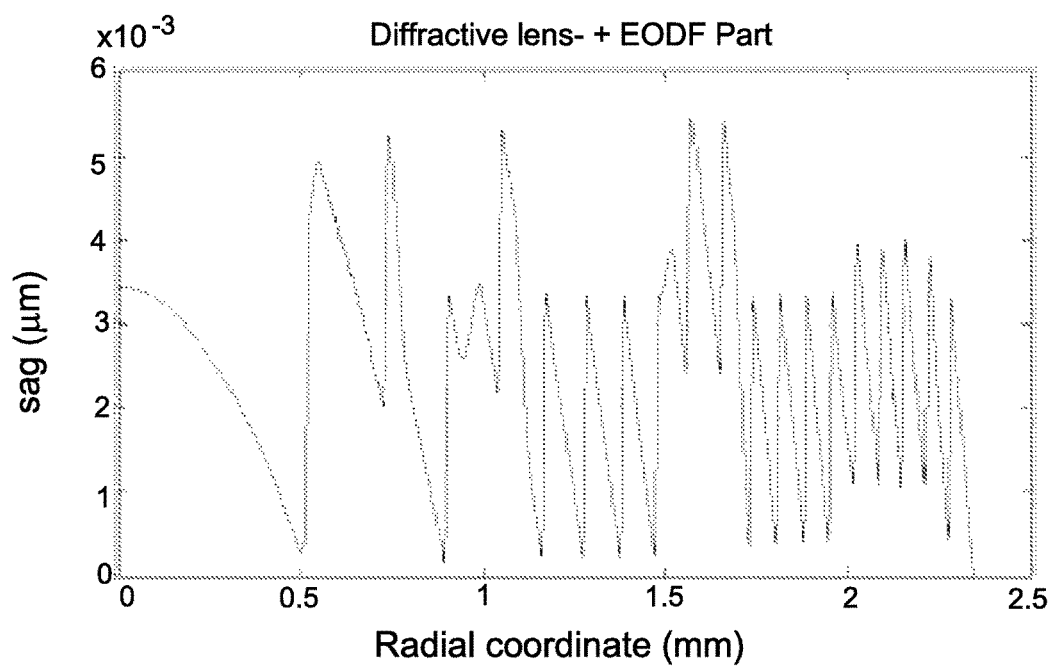

Reference is made to FIGS. 3A-3C exemplifying the effect of the optical processor according to the light field coding technique of the invention. FIG. 3A exemplifies a radial profile of the EDOF phase coding pattern PC (mask), which is a phase only, substantially not diffractive pattern designed to provide a desired EDOF profile for the imaging lens unit. FIG. 3B exemplifies a radial profile of the dispersion profile coding pattern DC, which is a diffractive pattern designed in accordance with the imaging lens with the EDOF profile to desirably shift the EDOF components of different wavelengths within said desired profile. FIG. 3C shows a combined coding (pattern) applied to the light field propagating in the imaging lens arrangement.

Let us consider the above coding of the imaging lens unit similar to that of the example of FIGS. 1A-1B. The function of the chromatic aberrations corrector (dispersion profile coder), configured for properly shifting the EDOF TFMTF plots, is implemented by a diffractive element (e.g. Fresnel lens).

Diffractive lens focal length, $f_{Diff}$, has the following wavelength dependency:

$$f_{Diff} = \frac{\lambda_0 f_0}{\lambda}$$

$$P_{Diff} = \frac{1}{f_{Diff}} = \frac{\lambda}{\lambda_0 f_0}$$

where $f_0$ is the focal length for a central wavelength $\lambda_0$.

Figure 4A:
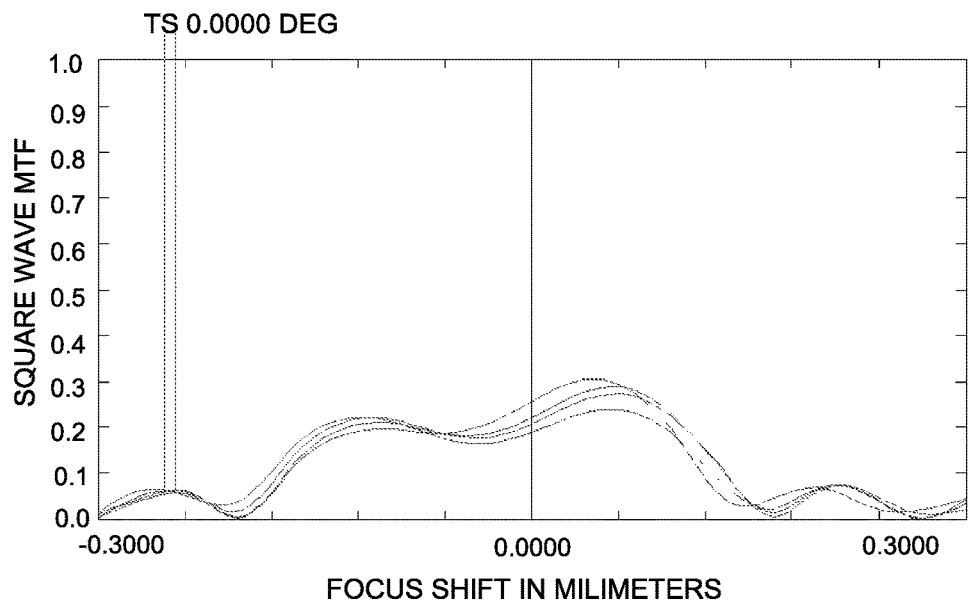
FIGS. 4A to 4D show simulation results for the TFMTF of the imaging lens arrangements of the present invention.
Figure 4B:
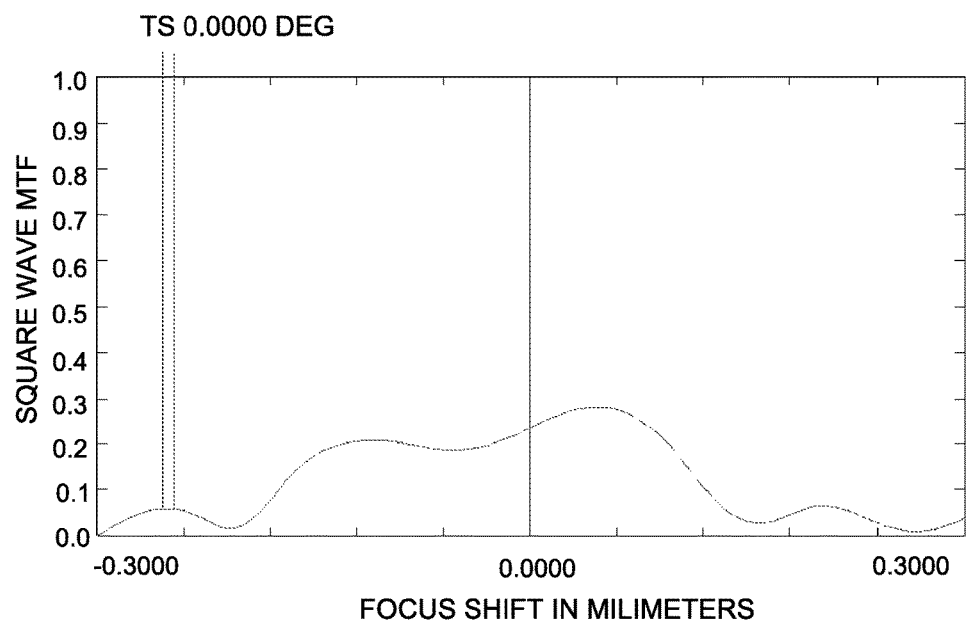

FIG. 4A shows that application of the appropriately designed diffraction pattern to the EDOF imaging lens provides that the TFMTFs for multiple wavelength are well co-aligned (generally desirably overlap), giving a desired total TFMTF. The latter is shown in FIG. 4B.

The diffractive lens 18 used for dispersion profile coding was simulated as made of PMMA material with total thickness, $T_{thick}$, determined as:

$$T_{thick} = \frac{\lambda}{n_{pmma} - n_{air}}$$

$n_{pmma}$ and $n_{air}$ being respective refractive indices. The optical power of such diffractive lens is determined as that of refractive plano-convex lens having power, and in the present example is:

$$P_{diff} = \frac{(n_{pmma} - n_{air})}{R} = 3.33 Diopt$$

where R=150 mm is the radius of the plano-convex refractive lens carrying the above described diffractive pattern. In this example, the diffractive lens is configured for ophthalmic application considering the optical power of the eye lens.

Figure 4C:
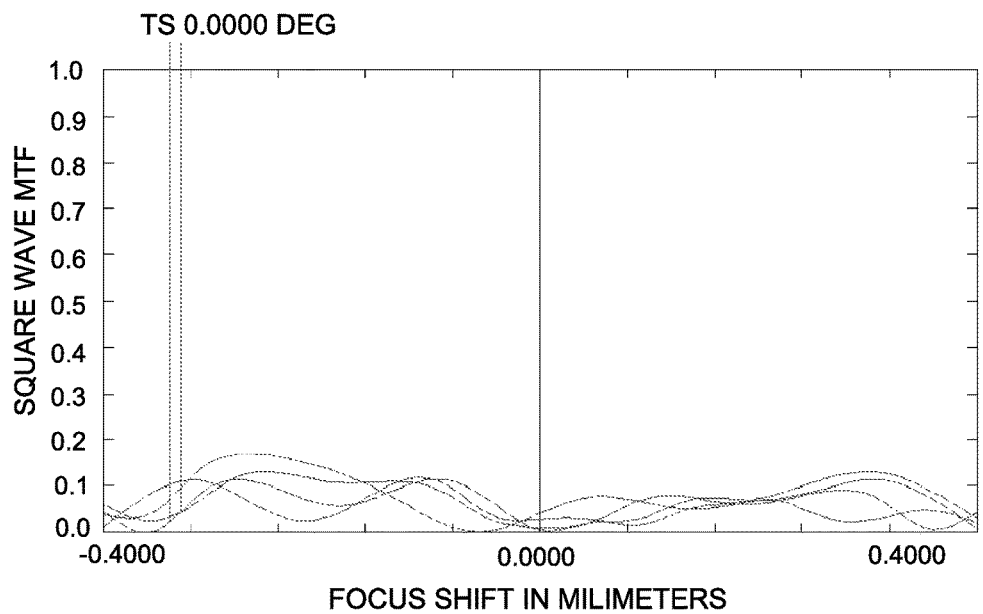
Figure 4D:
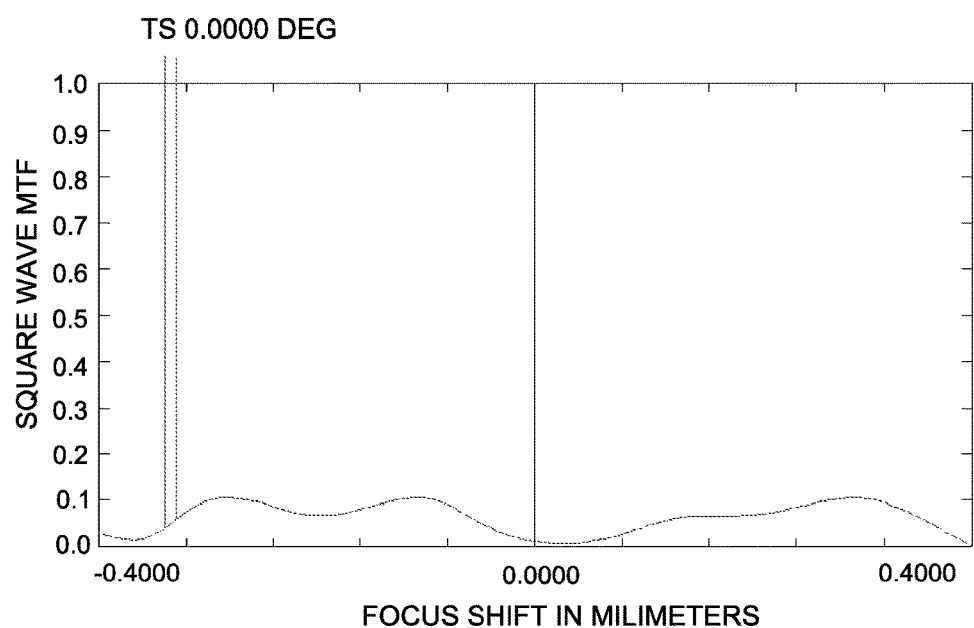

FIGS. 4C and 4D show similar simulation results for the bi-focal lens where an EDOF pattern was added to the bi-focal diffractive lens. As can be seen from the figures, the depth of focus is extended around each focus of the diffractive bifocal lens (attached to eye model) relative to the narrow depth of focus seen in FIGS. 1C and 1D.

Lenses as described herein can be used in ophthalmic applications, as a being a spectacles lens or a lens embodied as any suitable ophthalmic lens. The term "ophthalmic lens" refers to an artificial lens for use with the eye. Preferred ophthalmic lenses are made of biomedical materials suitable for contact with eye tissue. The term "ophthalmic lens" includes but is not limited to intraocular lenses (IOLs), contact lenses, and corneal onlays or inlays (intracorneal lenses).

It will be appreciated that non-optical components may be added in some embodiments of ophthalmic lenses (e.g., in intraocular lenses, one or more haptics may be added). Lenses according to aspects of the present invention can comprise combinations of surfaces having any suitable shape (piano, convex, concave). The illustrated embodiments of lenses have only one zone; however, other embodiments may have multiple zones, the zones having different optical powers.

In some embodiments, the lenses may be embodied as intraocular lenses adapted to provide accommodative movement. For example, a lens according to aspects of the present invention can be used in a dual element accommodative lens as described in U.S. Pat. No. 6,488,708 issued Dec. 4, 2002, to Sarfarazi, or a single element accommodative lens as described in U.S. Pat. No. 5,674,282, issued Sep. 7, 1997, to Cumming.

A pattern may be placed on a surface of the lens by various techniques known in the art. As a first example, the pattern may be lathe cut, lased or etched directly into the lens surface. As a second example, the pattern may be provided on a mold having a molding surface for forming the lens surface, wherein the pattern is transferred to the mold during casting of the lens. For example, a conventional manner of making contact lenses involves casting a mixture of lens-forming monomers in a two-part plastic mold. One mold part includes a molding surface for forming the front lens surface, and the second mold part includes a molding surface for forming the back lens surface. The monomer mixture is polymerized, or cured, while in the two-part mold to form a contact lens. The plastic mold parts are injected molded from a metal tool. For such a method, the pattern may be provided on the metal tools, such as by lathing, and thus transferred to the contact lens surface during the casting process.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

The invention claimed is:

1. An optical imaging arrangement, comprising:
    an optical imaging element for acting upon light comprising visible wavelengths;
    a phase coder associated with the optical imaging element; and a dispersion coder associated with the optical imaging element, the phase coder comprising a first pattern of features that induces a non-diffractive phase effect to the light comprising visible wavelengths, the first pattern of features comprising a first number of oscillations between radial coordinates of 0.5 mm and 2 mm, the phase coder providing additional depth of focus in addition to a depth of focus of the optical imaging element, the dispersion coder comprising a second pattern of features that induces a diffractive effect to the light comprising visible wavelengths, the second pattern of features comprising a second number of oscillations between radial coordinates of 0.5 mm and 2 mm, the second number of oscillations being greater than the first number of oscillations, the dispersion coder providing focus shifts of through focus modulation transfer function (TFMTF) profiles associated with the optical imaging element and the phase coder for multiple wavelengths of the light comprising visible wavelengths so as to increase an amount of overlap of the TFMTF profiles for the multiple wavelengths.

2. The optical imaging arrangement of claim 1, wherein the optical Imaging element comprises a lens.

3. The optical imaging arrangement of claim 1, wherein the phase coder provides the additional depth of focus without adding optical power beyond that of the optical imaging element.

4. The optical imaging arrangement of claim 1, wherein the phase coder provides the additional depth of focus without reducing an aperture of the optical imaging element.

5. The optical imaging arrangement of claim 1, wherein the phase coder provides the additional depth of focus without causing loss of energy.

6. The optical imaging arrangement of claim 1, wherein the phase coder provides the additional depth of focus without causing loss of resolution.

7. The optical imaging arrangement of claim 1, wherein the dispersion coder provides chromatic aberration correction.

8. The optical imaging arrangement of claim 1, wherein the first pattern is a radial pattern and the second pattern is a radial pattern.

9. The optical imaging arrangement of claim 1, wherein the first and second patterns are located at first and second sur aces, respectively, of the optical imaging element.

10. The optical imaging arrangement of claim 1, wherein the first and second patterns are in the form of first and second surface reliefs, respectively.

11. The optical imaging arrangement of claim 1, wherein the first and second patterns are incorporated in the optical imaging element.

12. The optical imaging arrangement of claim 1, wherein one of the first and second patterns is incorporated in the optical imaging element, and the other of said first and second patterns comprises a mask located at a side of the optical imaging element.

13. The optical imaging arrangement of claim 1, wherein the first and second patterns are disposed at a same surface and define together a combined pattern comprising a superposition of said first and second patterns.

14. The optical imaging arrangement of claim 1, wherein the optical imaging arrangement is configured as a lens.

15. The optical imaging arrangement of claim 1, wherein the imaging arrangement is configured as an ophthalmic lens.

16. The optical imaging arrangement of claim 15, wherein the ophthalmic lens is a multi-focal lens.

17. The optical imaging arrangement of claim 1, wherein the imaging arrangement is configured as a contact lens.

18. The optical imaging arrangement of claim 17, wherein the contact lens is a multi-focal lens.

19. The optical imaging arrangement of claim 1, wherein the optical imaging arrangement comprises multiple zones having different optical powers.

20. The optical imaging arrangement of claim 1, wherein the first pattern of features of the phase coder comprises three oscillations between radial coordinates of 0.5 mm and 2 mm, and wherein the second pattern of features of the dispersion coder comprises seven oscillations between radial coordinates of 0.5 mm and 1.5 mm.

* * * * *